United States Patent
Bosetto et al.

(10) Patent No.: US 7,074,191 B2
(45) Date of Patent: Jul. 11, 2006

(54) METHOD AND DEVICE FOR NON-INTRUSIVE MEASUREMENT OF BLOOD PRESSURE IN A CIRCUIT OF A DIALYSIS MACHINE

(75) Inventors: Antonio Bosetto, Mirandola (IT); Annalisa Delnevo, Sant'Agata Bolognese (IT)

(73) Assignee: Gambro Lundia AB, Lund (SE)

( * ) Notice: Subject to any disclaimer, the term of this patent is extended or adjusted under 35 U.S.C. 154(b) by 300 days.

(21) Appl. No.: 10/479,796

(22) PCT Filed: May 16, 2002

(86) PCT No.: PCT/IB02/01775

§ 371 (c)(1),
(2), (4) Date: Dec. 5, 2003

(87) PCT Pub. No.: WO02/098492

PCT Pub. Date: Dec. 12, 2002

(65) Prior Publication Data
US 2004/0144724 A1    Jul. 29, 2004

(30) Foreign Application Priority Data
Jun. 5, 2001    (IT)    .................. BO2001A0355

(51) Int. Cl.
*A61B 5/021*    (2006.01)
*G01L 9/00*    (2006.01)
*G01L 7/00*    (2006.01)
*A61M 1/14*    (2006.01)
*B01D 61/28*    (2006.01)

(52) U.S. Cl. .................. 600/488; 73/702; 73/705; 73/728; 73/730; 210/90; 600/486

(58) Field of Classification Search ................ 210/646, 210/741, 90, 97; 600/486, 488, 561; 73/705, 73/706, 707, 723, 728, 730, 751, 753, 702, 73/703; 250/559.29, 559.32, 559.39, 200, 250/591
See application file for complete search history.

(56) References Cited

U.S. PATENT DOCUMENTS

| | | | | |
|---|---|---|---|---|
| 3,842,353 A | * | 10/1974 | Stewart | 324/109 |
| 4,148,314 A | * | 4/1979 | Yin | 604/6.11 |
| 4,322,979 A | | 4/1982 | Fromm | |
| 4,324,663 A | * | 4/1982 | Hirel et al. | 210/646 |
| 4,428,239 A | * | 1/1984 | Johnston | 73/705 |
| 4,620,093 A | * | 10/1986 | Barkhoudarian et al. | 250/231.19 |

(Continued)

FOREIGN PATENT DOCUMENTS

EP    0 985 911 A2    3/2000

(Continued)

*Primary Examiner*—John S. Kim
(74) *Attorney, Agent, or Firm*—Finnegan, Henderson, Farabow, Garrett & Dunner, L.L.P.

(57) ABSTRACT

A method for the non-intrusive measurement of blood pressure in a circuit of a dialysis machine, using a device provided with a sleeve forming a portion of the blood circuit and having at least one part which moves according to the pressure difference between the inside and the outside of the sleeve, and with an emitter and a receiver of electromagnetic waves. The method comprising the emission of a beam of electromagnetic waves and the receiving of a beam of electromagnetic waves reflected from the moving part, in order to measure the displacement of the moving part in such a way as to establish a relationship between the position of the moving part and the pressure of the blood circulating in the sleeve.

14 Claims, 2 Drawing Sheets

U.S. PATENT DOCUMENTS

| | | |
|---|---|---|
| 5,000,049 A | 3/1991 | Cooper et al. |
| 5,158,091 A * | 10/1992 | Butterfield et al. ......... 600/485 |
| 5,410,916 A | 5/1995 | Cook |
| 6,005,242 A | 12/1999 | Chernyak |
| 6,171,253 B1 | 1/2001 | Bullister et al. |

FOREIGN PATENT DOCUMENTS

| | | |
|---|---|---|
| RU | 2 114 550 C1 | 7/1998 |

* cited by examiner

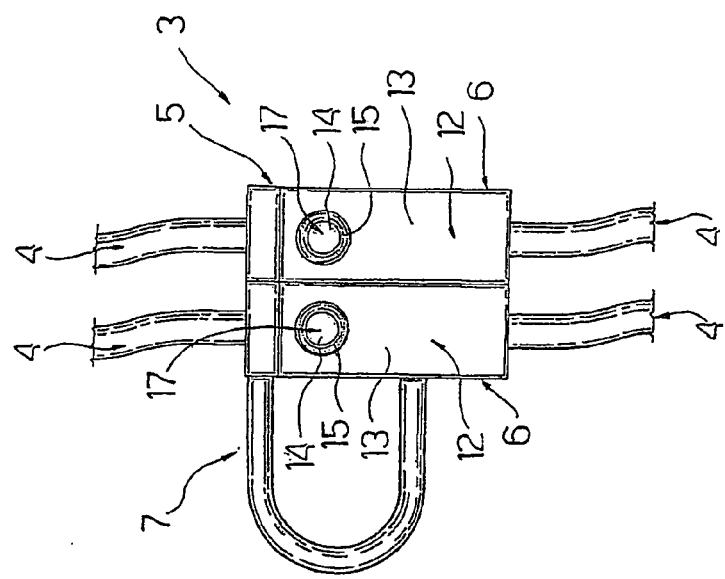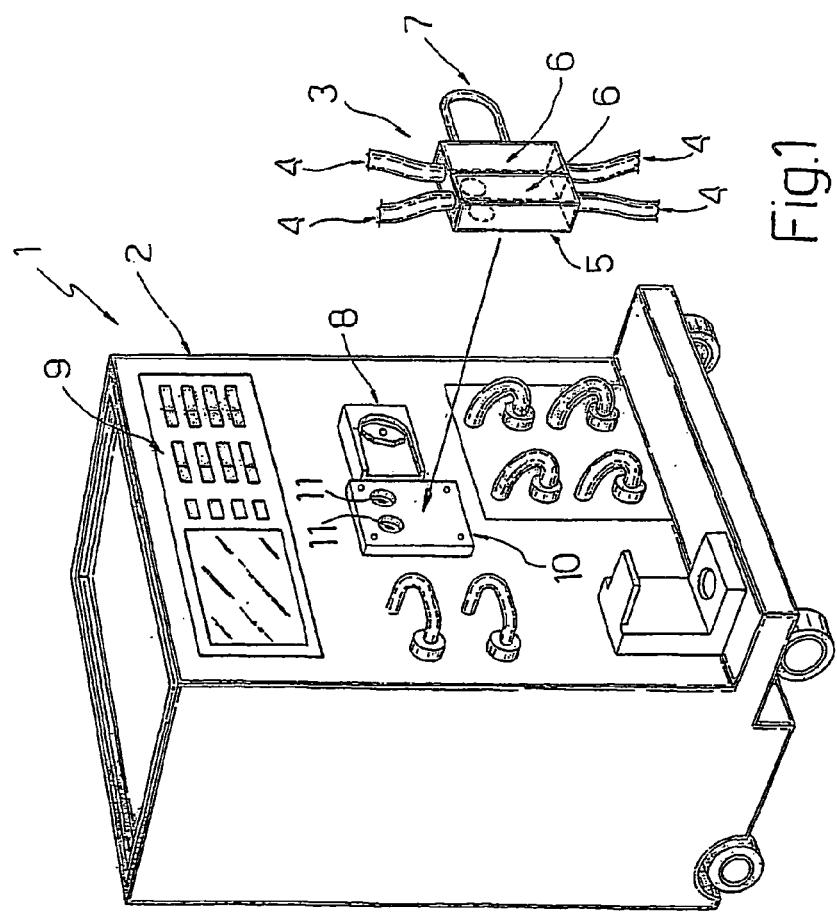

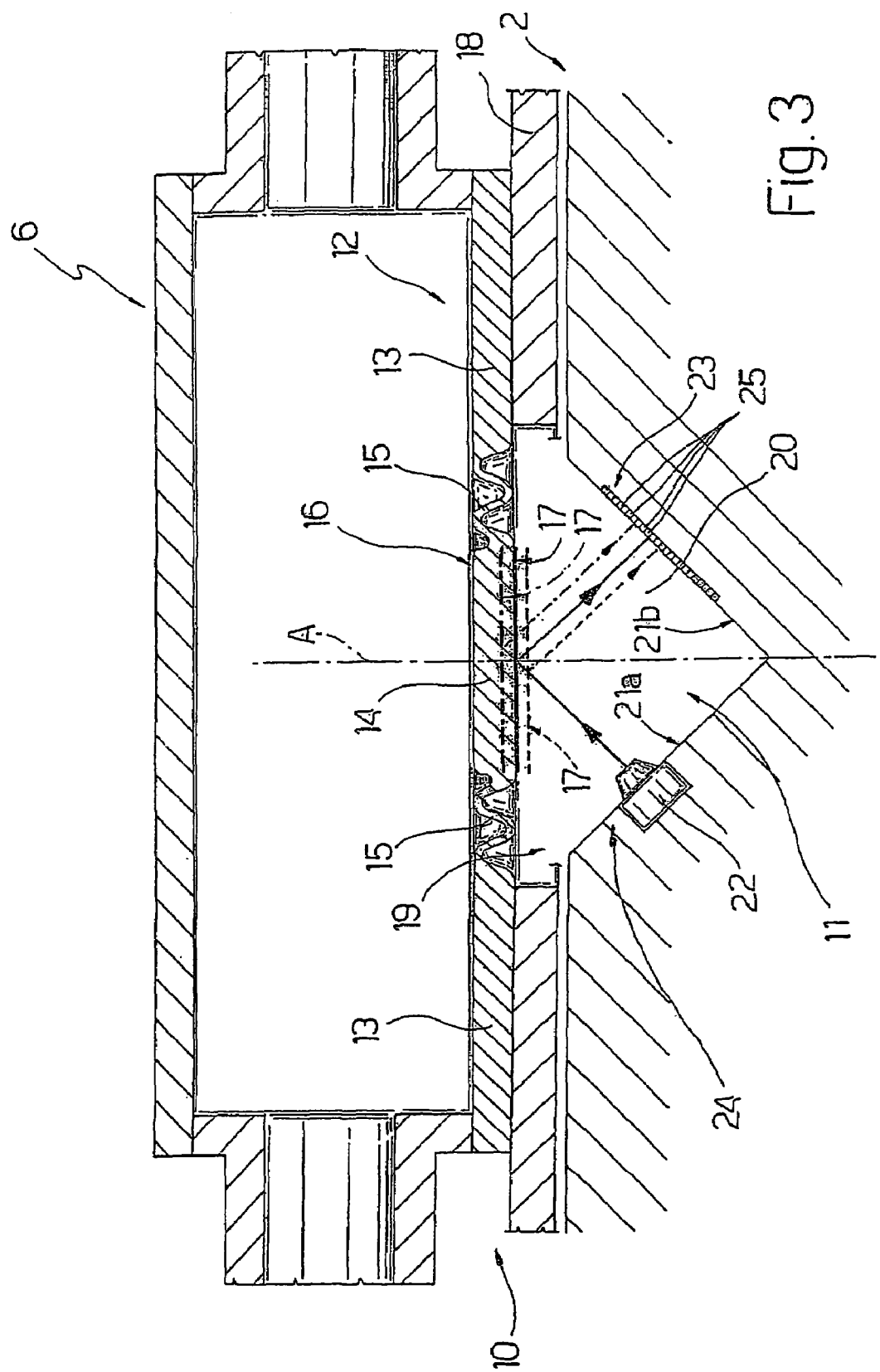

METHOD AND DEVICE FOR NON-INTRUSIVE MEASUREMENT OF BLOOD PRESSURE IN A CIRCUIT OF A DIALYSIS MACHINE

DESCRIPTION

The present invention relates to a method for the non-intrusive measurement of blood pressure in a circuit of a dialysis machine.

A dialysis machine of the known type comprises a machine casing, to which are connected a first circuit for blood circulation and a second circuit for the circulation of dialysate. The first and second circuits are connected to a filter so that the blood and the dialysate respectively can be directed through the filter, which is provided with a semi-permeable membrane which, when in use, separates the blood from the dialysate.

There is a known way of measuring blood pressure in a non-intrusive way in the first circuit of a machine of this type, by means of a measuring device having a sleeve which forms a portion of the first circuit and comprises a membrane which is elastic, and therefore sensitive to the pressure of the blood circulating in the sleeve, and a sensor fitted on the machine casing. In a first method of non-intrusive measurement of the blood pressure, the sleeve is fixed to the machine at the position of the sensor in such a way as to form a sealed chamber, inside which the aforesaid sensor is located in order to directly measure the pressure of the air contained in the sealed chamber and, consequently, the blood pressure. This method provides a satisfactory measurement of the blood pressure and can measure pressures which are either positive or negative, in other words below the ambient pressure. However, this method has the disadvantages of requiring a precise fitting of the sleeve in the housing and the maintenance of the sealing of the chamber throughout the dialysis treatment.

To overcome this drawback, an alternative method proposes the measurement of the force exerted on the membrane by the blood. To implement the aforesaid method of non-intrusive measurement of the blood pressure, it is necessary to use a device comprising a force sensor and a force transmitter positioned in a housing in the machine. The sleeve is coupled to the aforesaid housing in such a way that the force transmitter is placed between the force sensor and the membrane, and is in direct contact with both the force sensor and the membrane. This method does not require the formation of a sealed chamber, but cannot provide negative pressure values.

In order to measure negative pressure values, the membrane is pre-compressed against the force transmitter while the sleeve is being connected to the machine. However, the degree of pre-compression is affected by play in the connection, which can give rise to pre-compression errors and consequent measurement errors.

An alternative method of measuring negative pressure values consists in connecting the membrane to the force transmitter, for example by means of a magnet integral with the membrane. However, this procedure also has drawbacks, since it complicates the membrane and the sensor, which has to operate in tension and not only in compression.

The object of the present invention is to provide a method for the non-intrusive measurement of the blood pressure in a circuit of a dialysis machine, which overcomes the drawbacks of the known art, and which, at the same time, provides accurate measurements of the pressure and is simple to manufacture and use.

According to the present invention, a method is provided for the non-intrusive measurement of the blood pressure in a circuit of a dialysis machine, by means of a sleeve forming a portion of the said circuit and comprising a part which moves according to the pressure difference between the inside and the outside of the sleeve, the method being characterized in that a beam of electromagnetic waves is directed towards the said moving portion and the beam reflected from the said moving portion is received to determine the displacement of the moving portion with respect to a reference position of the moving portion.

The present invention also relates to a device.

According to the present invention, a device is provided for the non-intrusive measurement of the blood pressure in a circuit of a dialysis machine, the device comprising a sleeve provided with a part which moves according to the pressure difference between the inside and the outside of the sleeve, the device being characterized in that it comprises an emitter of a beam of electromagnetic waves and a receiver of a beam of electromagnetic waves reflected from the moving part to measure the displacements of the said moving part with respect to a reference position of the moving part.

BRIEF DESCRIPTION OF THE DRAWINGS

The present invention will now be described with reference to the attached drawings, which show a non-restrictive example of embodiment in which:

FIG. 1 is a perspective view, with parts removed for clarity, of a dialysis machine comprising a device for implementing the method according to the present invention;

FIG. 2 is a lateral elevation, with parts removed for clarity and on an enlarged scale, of a detail of a circuit associated with the machine of FIG. 1; and FIG. 3 is a schematic sectional view, on an enlarged scale and with parts removed for clarity, of the detail of the circuit of FIG. 2 associated with the machine of FIG. 1.

DETAILED DESCRIPTION

With reference to FIG. 1, the number 1 indicates the whole of a dialysis machine comprising a machine casing 2 and a blood circuit 3 (illustrated only partially) which can be connected to the machine casing 2. The machine 1 can extract blood from a patient, carry out a dialysis treatment, and transfer the treated blood to the patient. The circuit 3 comprises tubes 4 made from transparent flexible material (generally PVC), and a box 5 made from rigid plastic material, comprising two sleeves 6.

Each sleeve 6 is connected to two tubes 4 of the circuit 3 in such a way that the sleeve 6 forms a portion of the circuit 3. One of the sleeves 6 is also connected to a tube 7 which is bent into a U-shape and can interact with a rotor 8 associated with the machine 1 to form a peristaltic pump.

The machine casing 2 comprises, in addition to the rotor 8, a processing and control unit 9, and a mounting 10 for fixing the box 5, sensors 11 being fitted in this mounting.

With reference to FIG. 2, the box 5 is made, for example, from polycarbonate or polypropylene or other plastic material. Each sleeve 6 forms an internal compartment in the form of a parallelepiped and has a wall 12, which has two essentially rigid parts 13 and 14 and a flexible part 15 for connection between the portions 13 and 14. With reference to FIG. 3, the parts 13, 14 and 15 are made from the same material, but have different thicknesses. The part 13 is integral with the remaining parts of the sleeve 6 and is therefore referred to as fixed; it has a constant thickness, and is essentially rigid. The part 14 is referred to as moving, since it can be displaced with respect to the part 13 and has a circular shape and essentially the same thickness as the part 13, and is essentially rigid. The part 15 is very thin by comparison with the thickness of parts 13 and 14, and has an annular shape, concentric with the part 14. The part 15 also has a corrugated profile to permit the deformation of the part 14 with respect to the part 13. The part 14 has an inner face 16 and an outer face 17, which, when in use, interacts with one of the sensors 11.

With reference to FIGS. 1 and 3, each mounting 10 is formed by a fixing plate 18 for fixing the box 5 in a known way which is not illustrated in the attached figures, and for placing the box 5 in a specified position with respect to the machine casing 2. The plate 18 has two circular apertures 19 for access to corresponding recesses 20, within which the corresponding sensors 11 are housed. With reference to FIG. 3, each part 14 is positioned before a corresponding aperture 19 during the connection of the box 5 to the plate 18, in such a way as to cover a corresponding recess 20.

Each recess 20 has an axis A which is perpendicular to the plate 18 and consequently perpendicular to the face 17, and two walls 21a and 21b which are inclined with respect to the axis A. Each sensor 11 comprises an emitter 22, which is positioned on the wall 21a and is orientated in such a way as to direct a beam of electromagnetic waves towards the face 17 at an angle α of inclination with respect to the face 17, and a receiver 23, which is positioned on the wall 21b to receive a reflected beam of electromagnetic waves, which forms an angle α with respect to the face 17 on the opposite side to the emitted beam. The position of the reflected beam and, consequently, the area of incidence of the reflected beam on the receiver 23 are modified by the position of the face 17 of the portion 14 as shown in broken lines and in chained lines in FIG. 3.

In practice, each sleeve 6 and each sensor 11 jointly form a device 24 for measuring the position of the part 14 with respect to the part 13, and consequently the blood pressure in the circuit 3.

For this purpose, the receiver 23 is formed from a sequence of adjacent cells 25, each of which sends a signal when struck by the reflected beam. In the described embodiment, the electromagnetic waves are in the visible range and the cells are photosensitive cells 25. The emitter 22 and the receiver 23 are controlled by the unit 9, which processes the signals received from the receiver 23 to determine a value of blood pressure.

In use, the box 5 is fixed on the mounting 18 so that the parts 14 are positioned before the apertures 19 of the plate 18, as described above. Before the dialysis treatment is started, in other words when the circuit 3 is empty, a procedure of zero setting the measuring device 24 is carried out. This zero setting procedure consists in emitting a beam of electromagnetic waves by means of the emitter 22 and determining which cell 25 has received the reflected beam in the rest condition, in such a way that the unit 9 determines a match between the cell 25 which has received the reflected beam and the ambient pressure. In practice, in the zero setting stage, the pressure acting on the face 17 is equal to the pressure acting on the face 16, and the part 14 is in a rest position which is taken as the reference position of the portion 14. The dialysis treatment is then started, and during the treatment the blood flows through the circuit 3 and undergoes fluctuations of pressure, according to the operating conditions of the machine 1 and the characteristics of the patient, the pressure acting on the face 16 to cause displacements of the part 14 of the wall 12 with respect to the reference position. For example, in FIG. 3, the position of the face 17 of the wall 14 is indicated by a broken line, corresponding to an operating condition in which the blood in the circuit 3 has a pressure greater than the ambient pressure. In this stage, the point of incidence of the emitted beam along the outer face 17 moves closer to the emitter 22, and consequently the reflected beam shown in broken lines strikes a different photosensitive cell 25 from the cell 25 which is struck when the part 14 is in the reference position. The unit 9 receives the signal from the struck cell 25 and determines the blood pressure in accordance with a calibration carried out by an experimental procedure.

Similarly, when the blood circulating in the circuit 3 has a pressure below the ambient pressure, the face 17 assumes the position indicated by a chained line in FIG. 3, and is further away from the emitter 22 than it is in the rest condition. Consequently, the reflected beam is directed towards a photosensitive cell 25 which measures the new position of the face 17 and the unit 9 determines a corresponding value of blood pressure.

The described device 24 has the advantage of requiring relatively simple fitting and allows errors of fitting to be corrected automatically, by means of the zero setting procedure.

The invention claimed is:

1. A method for the non-intrusive measurement of blood pressure in a circuit of a dialysis machine, by means of a sleeve forming a portion of said circuit and comprising a part which moves according to a pressure difference between an inside and an outside of the sleeve, the method being characterized in that a beam of electromagnetic waves is directed toward said moving part and the beam reflected from said moving part is received in order to determine the displacement of the moving part with respect to a reference position of the moving part, said moving part being a rigid part of a wall of said sleeve and having an inner face which can be placed in contact with the blood circulating in said circuit.

2. A method according to claim 1, wherein the electromagnetic waves are in the visible spectrum.

3. A method according to claim 1, wherein said beam of electromagnetic waves is emitted by an emitter and received by a receiver, said emitter and said receiver being located on the dialysis machine.

4. A method according to claim 1, wherein an emitted beam is directed in such a way that said emitted beam is inclined with respect to an outer face of said moving part.

5. A method according to claim 1, wherein said beam of electromagnetic waves is emitted by an emitter and received by a receiver, said method further comprising a zero setting stage, in which said reference position of the moving part with respect to the emitter is determined, said stage of zero setting comprising associating at least one sensitive cell of the receiver with a known value of pressure within the sleeve; said reference position being determined for an operating condition in which the pressure acting on the outer face is equal to the pressure acting on the inner face.

6. A method according to claim 5, wherein said pressure is the ambient pressure; said stage of zero setting being implemented before a start of a dialysis treatment.

7. A device for the non-intrusive measurement of blood pressure in a circuit of a dialysis machine, the device comprising a sleeve provided with a part which moves according to the pressure difference between the inside and the outside of the sleeve, the device being characterized in that it comprises an emitter of a beam of electromagnetic waves and a receiver of a beam of electromagnetic waves reflected from the moving part to measure the displacements of said moving part with respect to a reference position of the moving part, said moving part being a rigid cart of a wall of said sleeve.

8. A device according to claim 7, wherein the emitter and the receiver are fitted on the dialysis machine in a mounting for receiving said sleeve.

9. A device according to claim 7, wherein said moving part has an inner face which can be placed in contact with the blood flowing within the circuit and an outer face which can reflect the emitted beam.

10. A device according to claim 7, wherein the wall comprises a rigid fixed part, said moving part and a flexible part for connecting said moving part to said fixed part.

11. A device according to claim 10, wherein the fixed part, the moving part, and the flexible part are made in one piece and from the same material.

12. A device according to claim 11, wherein the flexible part is thinner than the thickness of the fixed part and the moving part.

13. A device according to claim 12, wherein said moving part is circular, said flexible part being annular and concentric with the moving part.

14. A device according to claim 13, wherein said flexible part is corrugated.

* * * * *

UNITED STATES PATENT AND TRADEMARK OFFICE
CERTIFICATE OF CORRECTION

| | | |
|---|---|---|
| PATENT NO. | : 7,074,191 B2 | Page 1 of 1 |
| APPLICATION NO. | : 10/479796 | |
| DATED | : July 11, 2006 | |
| INVENTOR(S) | : Antonio Bosetto and Annalisa Delnevo | |

It is certified that error appears in the above-identified patent and that said Letters Patent is hereby corrected as shown below:

In claim 7, column 5, line 4, "cart" should read --part--.

Signed and Sealed this

Third Day of October, 2006

JON W. DUDAS
*Director of the United States Patent and Trademark Office*